US011672558B2

(12) United States Patent
Voic

(10) Patent No.: US 11,672,558 B2
(45) Date of Patent: Jun. 13, 2023

(54) ULTRASONIC SPINAL SURGERY METHOD

(71) Applicant: MISONIX, INCORPORATED, Farmingdale, NY (US)

(72) Inventor: Dan Voic, Cedar Grove, NJ (US)

(73) Assignee: MISONIX, LLC, Farmingdale, NY (US)

( * ) Notice: Subject to any disclaimer, the term of this patent is extended or adjusted under 35 U.S.C. 154(b) by 11 days.

(21) Appl. No.: 17/326,617

(22) Filed: May 21, 2021

(65) Prior Publication Data

US 2022/0370092 A1 Nov. 24, 2022

(51) Int. Cl.
*A61B 17/32* (2006.01)
*A61B 17/16* (2006.01)

(52) U.S. Cl.
CPC .. *A61B 17/320068* (2013.01); *A61B 17/1671* (2013.01); *A61B 2017/320073* (2017.08); *A61B 2017/320082* (2017.08)

(58) Field of Classification Search
CPC .............................................. A61B 17/320068
See application file for complete search history.

(56) References Cited

U.S. PATENT DOCUMENTS

| | | | | |
|---|---|---|---|---|
| 2002/0049462 | A1* | 4/2002 | Friedman ....... | A61B 17/320068 606/169 |
| 2003/0191474 | A1* | 10/2003 | Cragg ................ | A61B 17/3203 606/79 |
| 2006/0095046 | A1* | 5/2006 | Trieu ................. | A61B 17/1671 606/99 |
| 2008/0300591 | A1* | 12/2008 | Darian ........... | A61B 17/320068 606/41 |
| 2015/0142033 | A1* | 5/2015 | Stulen ............ | A61B 17/320068 606/169 |

* cited by examiner

*Primary Examiner* — Christian A Sevilla
(74) *Attorney, Agent, or Firm* — R. Neil Sudol; Henry D. Coleman

(57) ABSTRACT

In a surgical method, an elongate probe is inserted into a spinal disc exemplarily into a nucleus pulposus thereof in a direction generally parallel to vertebral end faces adjacent to the spinal disc. During the inserting of the elongate probe, the probe is ultrasonically vibrated. Thereafter, while ultrasonically vibrating the elongate probe, one moves the elongate probe to sever a prismatic portion of the spinal disc including a prismatic section of the nucleus pulposus. The prismatic portion of the spinal disc is removed from a remaining portion of the spinal disc.

18 Claims, 1 Drawing Sheet

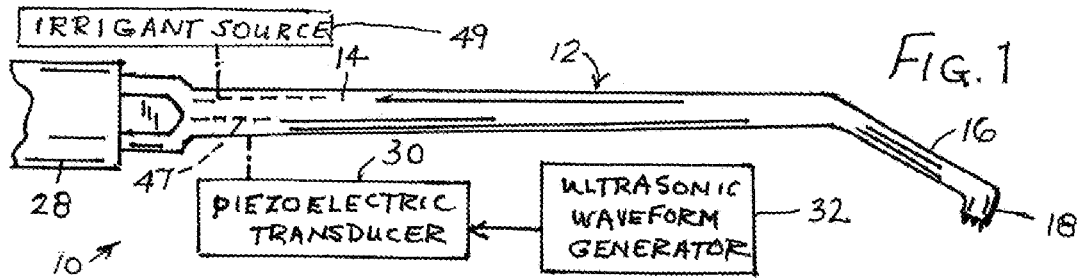
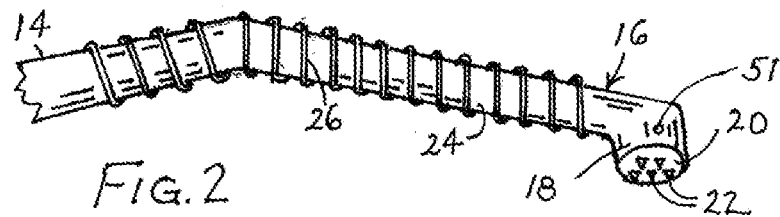
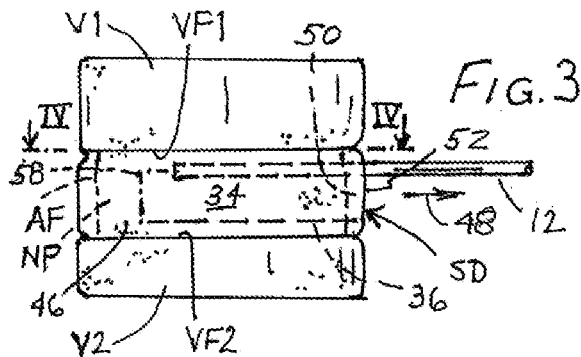
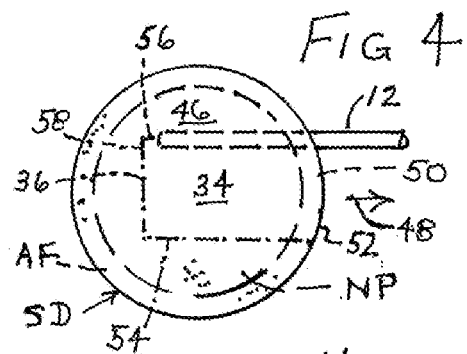
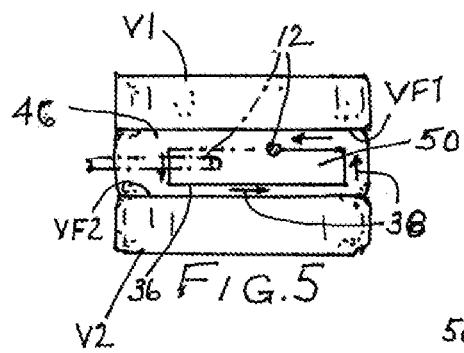
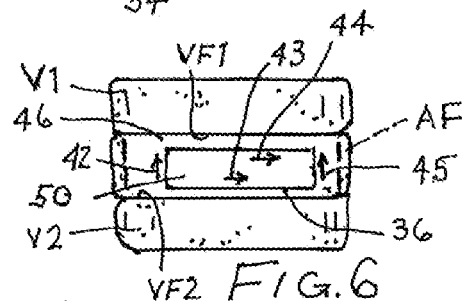
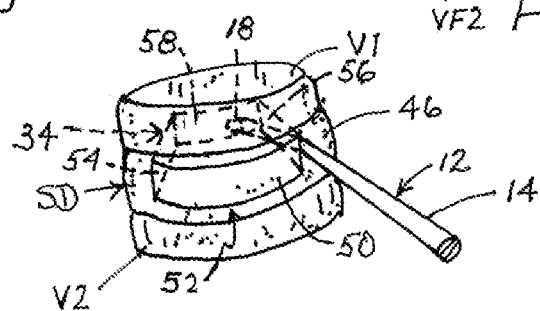

ULTRASONIC SPINAL SURGERY METHOD

BACKGROUND OF THE INVENTION

This invention relates to surgical procedures commonly known as discectomy and nucleotomy.

The spinal column is comprised in part of bones or vertebrae and in part of fibrous discs that are disposed between the vertebrae. The discs normally function as cushions separating the vertebrae. With age, owing to a drying of the discs, the cushioning effect may be reduced. Also injury can cause a disc to bulge and press on the nerve root leaving the spinal column, possibly causing extreme pain.

More specifically, when the outer wall of a disc, called the annulus fibrosus, becomes weakened through age or injury, it may tear allowing the soft inner part of the disc, the nucleus pulposus, to bulge out. This is called disc herniation, disc prolapse, or a slipped or bulging disc. Once the inner disc material extends out past the regular margin of the outer disc wall, it can press against very sensitive nerve tissue in the spine. The "bulging" disc can compress or even damage the nerve tissue, and this can cause weakness, tingling, or pain in the back area and into one or both legs. The nerve compression can also lead to bowel and bladder dysfunction.

A discectomy is a surgical procedure generally to remove part of an intervertebral disc that is putting pressure on a nerve as it leaves the spinal column. The procedure is most commonly performed on lumbar discs (located in the lower back) creating leg pain. However, it may also be used for cervical discs in the neck.

Open discectomy is usually performed under general anesthesia (the patient is unconscious) and typically requires a one-day hospital stay. It is performed while the patient is lying face down or in a kneeling position. During the procedure, the surgeon will make an approximate one-inch incision in the skin over the affected area of the spine. Muscle tissue is removed from the bone above and below the affected disc and retractors hold the muscle and skin away from the surgical site so the surgeon has a clear view of the vertebrae and disc. In some cases bone and ligaments may have to be removed for the surgeon to be able to visualize and then gain access to the bulging disc without damaging the nerve tissue, this is called a laminectomy or laminotomy depending on how much bone is removed.

Once the surgeon can visualize the vertebrae, disc and other surrounding structures, he or she will remove the section of the disc that is protruding from the disc wall and any other disc fragments that may have been expelled from the disc. This is often done under magnification.

Current discectomy and disc space preparation procedures entail the use of a sharp Blade for annulus incision, a Pituitary Rongeur for initial access and removal of a nucleus pulposus, a curette to free up disc material, and a Pituitary Rongeur for disc material removal, a rasp for end plate preparation. Ideally the number of instruments and instrument passes in and out of the disc space should be minimized.

In treating a bulging disc, typically no material is used to replace the disc tissue that is removed. The incision is closed with sutures and the patient is taken to a recovery room. In a disc space preparation procedure, a prosthesis such as a spinal cage is inserted into the disc space upon completion of a partial or complete discectomy. In such a discectomy, enough disc material is removed to enable the deployment of the prosthesis. The opposing vertebral endplate surfaces are cleaned of soft tissue to enable prosthesis attachment or fusion with the vertebral bone tissue.

The most common problem of a discectomy is that there is a chance that another fragment of disc will herniate and cause similar symptoms down the road. This is a so-called recurrent disc herniation, and the risk of this occurring is about 10-15%.

OBJECTS OF THE INVENTION

It is an object of the present invention to provide an improved approach for a discectomy procedure particularly a procedure that removes all or a substantial portion of a spinal disc in preparation of the disc space for reception of a prosthesis such as a vertebral fusion cage. In many cases, the invention anticipates removal of an entire disc including the nucleus, the annulus and osteophytes.

It is another object of the present invention to provide an improved approach for a disc space preparation procedure. The present invention aims at providing a surgical disc space preparation procedure that is at least partially quicker, more complete, and easier to carry out than conventional techniques. The present invention additionally contemplates a surgical disc space preparation procedure that may be performed minimally invasively.

It is a related object of the present invention to provide an improved procedure for a nucleotomy, the removal of a nucleus of a spinal disc, or a partial nucleotomy.

Another object of the present invention is to provide a surgical discectomy or nucleotomy method that is at least partially quicker and easier to carry out than conventional techniques.

Yet another object of the present invention is to provide a surgical discectomy or nucleotomy method that may be carried out in a minimally invasive procedure.

It is an additional object of the present invention to provide a surgical discectomy or nucleotomy method that reduces, if not minimizes, the number of instruments and instrument passes in and out of the disc space.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

The present invention provides a discectomy method as part of a disc space preparation procedure, preparing a space between two vertebrae for installation of a prosthesis such as a vertebral fusion cage. In many cases, the invention anticipates removal of an entire disc including the nucleus, the annulus and osteophytes. Such a disc space preparation procedure preferably entails removal not only of all or a substantial portion of a spinal disc but also a removal of disc material, soft tissue and cartilage from vertebral endplate surfaces to enhance bonding between prosthesis and vertebrae. Incidental removal of bony tissue is preferably minimized to forestall the prosthesis from breaking through and into the vertebrae.

A surgical method comprises, in accordance with the present invention, (i) inserting an elongate probe into a spinal disc in a direction generally parallel to vertebral end faces adjacent to the spinal disc, (ii) during the inserting of the elongate probe, ultrasonically vibrating the probe, (iii) thereafter, while ultrasonically vibrating the elongate probe, moving the elongate probe to sever a prismatic portion of the spinal disc, and (iv) removing the prismatic portion from a remaining portion of the spinal disc.

Pursuant to other features of the present invention, the moving of the elongate probe includes moving the elongate probe along an endless path or perimeter partially defining the prismatic portion and preferably executing the probe motion while maintaining the probe in substantially parallel relation to the vertebral end faces.

The motion of the probe along the endless path or perimeter need not be continuous. On occasion it may be necessary or advisable to remove the probe from the disc space, from between adjacent vertebral endplates, and reinsert the probe at a different point. The end result of this operation is to separate a chunk of the spinal disc, including a portion of the nucleus pulposus and optionally a portion of the annulus fibrosus, along a perimeter, that is, along the endless path or perimeter.

Pursuant to a further feature of the present invention, the endless path or perimeter may extend in part through the annulus fibrosus of the spinal disc so that a portion of the annulus fibrosus is attached to a portion of the nucleus pulposus and is removed therewith from the remaining portion of the spinal disc.

The severed portion of the annulus fibrosus is typically coextensive with a prismatic part of the nucleus pulposus. In that case, the endless path or perimeter extends in continuous fashion through the annulus and the nucleus of the spinal disc. Moreover, the severing of the prismatic portion of the spinal disc is effectuated at least in part by the moving of the elongate probe along the one same path or perimeter while ultrasonically vibrating the elongate probe.

Typically, the elongate probe is inserted into the spinal disc material from one side of the spinal disc. The method may additionally comprise (a) after the moving of the elongate probe along the one common path or perimeter to sever the prismatic portion from the remaining portion along that path or perimeter, orienting the elongate probe at an acute angle with respect to a lateral surface of the prismatic portion, (b) inserting a distal shaft section of the probe under the prismatic portion, on a far or distal side thereof opposite the one side of the spinal disc, and (c) ultrasonically vibrating the elongate probe while the distal shaft section thereof is located under the prismatic portion, to thereby sever the far side of the prismatic nuclear portion at least in part from the remaining portion of the disc. The removal of the prismatic portion of the nucleus pulposus from the remainder of the disc may be accomplished in part by prying or levering the prismatic portion away from the remaining disc material with the elongate ultrasonic probe.

It is contemplated that the elongate probe is an asymmetric dissector-shaver which includes (1) a proximal shaft section, (2) a distal shaft section angled relative to the proximal shaft section, and (3) a head extending from a distal end of the distal shaft section laterally relative to the distal end section, the head having a distal end surface provided with knurls or teeth. The distal shaft section is advantageously provided along an outer surface with at least one energy concentrating projection, preferably in the form of a spiral rib.

The method contemplates severing a prismatic portion of the spinal disc that includes a portion of an annulus fibrosus of the spinal disc so that the severed annulus portion is attached to a prismatic nuclear portion and removed therewith from the remaining spinal disc material.

It is to be noted that subsequent to the removal of the prismatic nuclear portion, with or without an attached annulus section, the remaining disc material may itself be partially or completely removed in a continuing operation. For instance, the elongate ultrasonic probe may be operated to remove at least some, and preferably all, of the disc material as well as soft tissue and cartilage adhering to one or both of the opposing vertebral end faces. This procedure prepares the vertebral bone surfaces for receiving a graft or disc prosthesis between the bone surfaces. Thus the discectomy procedure described herein may constitute part of a disc space preparation procedure preparatory to inserting a prosthesis such as a vertebrae-fusing cage or a gel-filled sac into the disc space and into contact with the vertebral endplate surfaces. The cleaning of the endplate surfaces facilitates attachment of the prosthesis to the vertebral endplates. The ultrasonically vibrating of the ultrasonic instrument during the contacting of the vertebral endplates serves in part to provide the opposing faces with textured surfaces. The leveling and texturing of the vertebral surfaces opens access to the blood vessels in the vertebrae and facilitates subsequent growth and attachment of the bone to the material of a disc prosthesis or graft.

A channel or lumen in the probe shaft and an aperture in the probe head communicating therewith may be used in part to feed a cooling liquid to the probe head and particularly to knurled surfaces thereof during the severing of the prismatic portion of the spinal disc and during contacting of the opposing faces of the vertebrae. In addition, the channel or lumen may be used to aspirate the particulate matter formed during the ultrasonic disruption process. The inserting of the distal end of the probe into the spinal disc includes operating the instrument to form an opening in the annulus of the spinal disc and to penetrate through the opening into the disc.

The severed portion of the annulus fibrosus may be coextensive with and removed as one body with a prismatic portion of the nucleus pulposus.

Optionally, a different probe such as a flat ultrasonic blade may be used to cut through the annulus fibrosus. Such a probe may be used either to make only an initial cut or to make an endless incision defining an annulus section to be removed. However, in the interest of reducing the number of instruments and instrument passes in and out of the disc space, the surgeon is encouraged to use the same instrument, such as the asymmetric dissector-shaver described above, to perform multiple steps of the overall procedure, including annulus incision, initial access and removal of a chunk (prismatic portion) of nucleus pulposus, freeing up of disc material, disc material removal, and even at least partial end plate preparation.

BRIEF DESCRIPTION OF THE DRAWINGS

FIG. 1 is partially a block diagram and partially a schematic side elevational view of a probe used in a discectomy procedure in accordance with the present invention.

FIG. 2 is a schematic partial side elevational view of the probe of FIG. 1, on a larger scale.

FIG. 3 is a schematic side elevational view of a spinal disc and a pair of vertebral bones flanking the disc, showing a stage in discectomy procedure in accordance with the present invention.

FIG. 4 is a schematic top view of the disc of FIG. 3, taken along plane IV-IV in FIG. 3.

FIG. 5 is a schematic back elevational view of the disc and vertebrae of FIG. 3, showing an incision made in a discectomy procedure pursuant to the present invention and also showing another step in the procedure.

FIG. 6 is a view similar to that of FIG. 5, indicating an alternative incision sequence.

FIG. 7 is a schematic perspective view the disc and vertebrae of FIGS. 3, 5 and 6 showing the step of FIG. 5 and a prismatic volume of disc material formed by ultrasonic cutting pursuant to the invention.

DEFINITIONS

The term "discectomy" is used herein to designate a procedure involving removal of spinal disc material from a spinal disc between two vertebrae or vertebral endplates. The disc material being removed may be small, for instance, to prevent impingement of a spinal disc on the spinal cord. Alternatively, a discectomy may entail removal of a substantial portion of a disc, such as the nucleus pulposus, or an entire disc including both the pulposus and the annulus fibrosus.

A "disc space preparation" procedure pursuant to the present disclosure includes not only a substantial discectomy, or removal of a substantial portion or all of a spinal disc, but also contemplates preparation of the adjacent vertebral end faces so that a prosthesis inserted into the disc space between the two vertebral endplates satisfactorily adheres to the endplates. The preparation of the disc space includes cleaning or removal of disc material, soft tissue and cartilage from the vertebral end faces, thereby increasing the likelihood of proper adhesion of a prosthesis to the vertebrae. The cleaning of the endplate faces or surfaces typically results in possibly undesirable but unavoidable removal of osseous tissue. Vertebral osteophytes may be removed in the process. The use of an ultrasonic probe to clean vertebral endplates is advantageous in that little force need be applied to the vertebrae. Thus greater control is possible, enabling a surgeon to remove just enough disc material and cartilage to enable fusion of a prosthesis with the bony tissue, without unnecessarily increasing the chances of the prosthesis breaking through and rupturing the vertebral end face.

The term "probe" or "ultrasonic probe" is used herein to designate an elongate metallic tool designed to carry an ultrasonic standing wave of a predetermined ultrasonic frequency, so that an operative surface or edge at the distal end of the probe entertains a maximal movement amplitude at the predetermined ultrasonic frequency and a correspondingly maximized transmission of ultrasonic vibratory energy to a target organic tissue within a patient.

The term "major plane" is used herein to describe the plane transverse to an ultrasonic probe's longitudinal axis wherein the probe head is widest and thus has its greatest transverse dimension. The probe head preferably has a cutting edge, and more preferably two opposed cutting edges, disposed in the major (transverse) plane.

The term "laterally enlarged" is used herein to describe a probe head that is wider than the distal end of the probe shaft. The probe head projects to the side beyond the shaft, at least in part facilitating contact with vertebral endplate faces.

The term "prismatic portion" is used herein to designate a cohesive volume of spinal disc material including of the nucleus pulposus. The volume typically extends parallel to vertebral bone surfaces on opposing sides of a spinal disc constituting a surgical site.

DETAILED DESCRIPTION

FIGS. 1 and 2 depict an ultrasonic instrument for use in a discectomy procedure. The instrument comprises an asymmetric dissector-shaver 10 which includes an elongate probe 12 having a linear proximal shaft section 14, a linear distal shaft section 16 extending at an angle θ relative to the proximal shaft section 14, and a head 18 extending from a distal end (not designated) of the distal shaft section 16 laterally relative to the distal end section. Head 18 has a distal end surface 20 provided with knurls or teeth 22. Distal shaft section 16 is advantageously provided along an outer surface 24 with at least one energy concentrating projection 26, preferably in the form of a spiral rib.

Asymmetric dissector-shaver 10 includes a handle 28 housing a piezoelectric or magnetostrictive transducer 30 that converts an electrical waveform into an ultrasonic vibration that generates a standing waveform in probe 12. Transducer 30 is operatively connected to an ultrasonic waveform generator 32 that produces the electrical waveform and feeds the waveform to the transducer.

As illustrated in FIGS. 3-5, a surgical discectomy method entails inserting probe 12 into a a spinal disc SD, for instance, into a nucleus pulposus NP thereof, in a direction generally parallel to vertebral end faces VF1 and VF2 of vertebrae V1 and V2 adjacent to the spinal disc. During the inserting of elongate probe 12, waveform generator 32 and transducer 30 ultrasonically vibrate the probe. Thereafter, while probe 12 continues to ultrasonically vibrate, one moves the probe to sever a prismatic portion or volume 34 of the spinal disc SD, particularly a prismatic section of the nucleus pulposus NP. Preferably, but not necessarily, probe 12 is translated along an endless or continuous rectangular path 36 defining a lateral perimeter of the prismatic portion 34. Probe 12 may be moved continuously along rectangular path 36 as indicated by arrows 38 in FIG. 5. Alternatively, the motion of probe 12 along path or perimeter 36 need not be continuous. As shown in FIG. 6, prismatic portion 34 may be severed along path or perimeter 36 by translating probe 12 along different path portions 42-45 in various sequences, removing the probe from, and reinserting the probe into, the spinal disc SD as necessary or desired. In any event, elongate probe 12 is preferably moved along path or perimeter 36 while maintaining the probe in substantially parallel relation to vertebral end faces VF1 and VF2.

The end result of this operation is to separate a prismatic portion or chunk 34 of spinal disc SD, and particularly of the nucleus pulposus NP, along path or perimeter 36. Upon sufficient severing of prismatic portion 34, the prismatic portion is removed from a remaining portion 46 of spinal disc SD, as indicated by an arrow 48 (FIGS. 3 and 4).

Probe 12 is formed with a channel or lumen 47 that communicates with a pressurized supply 49 (FIG. 1) of cooling liquid or irrigant. The irrigant is typically conducted through the channel or lumen 47 from supply 49 during an ultrasonic surgical procedure and particularly during the energization of the probe 12 with ultrasonic mechanical vibratory energy generated by transducer 30 in response to an electrical waveform from generator 32. The irrigant exits the head 18 through one or more apertures 51 (FIG. 2). The irrigant serves in part to maintain the instrument and the tissues at thermal equilibrium during ultrasonic energization of the probe within the patient. The irrigant also serves to enable ultrasonic cavitation and to generate a slurry of disc and endplate surface particulates that may be extracted via aspiration.

Probe 12 may be inserted into nucleus pulposus NP of spinal disc SD through an annulus fibrosus AF on a rear side 52 of the spinal disc and the adjacent vertebra V1, V2 and manipulated to sever a prismatic section 50 of the annulus fibrosus continuous with and attached to prismatic portion 34 of the nucleus pulposus NP. Prismatic annulus section 50 is removed from the patient's spinal column (not separately shown) integrally with prismatic nuclear portion 34.

Alternatively, an initial incision made be formed in annulus fibrosus AF by a different instrument such as an ultrasonic ablation blade or rotary cutter. This initial incision may be called for where the annulus fibrosus AF is tough or resistant to penetration by probe 12. Preferably, however, ultrasonic probe 12 is used to sever both prismatic section 50 of annulus fibrosus AF and prismatic portion 34 of nucleus pulposus NP simultaneously in the same operation. In other words, the cutting of prismatic portion 34 around path or perimeter 36 also cuts prismatic section 50 around the same path or perimeter. Severed section 50 of annulus fibrosus AF is then coextensive with prismatic portion 34 of nucleus pulposus NP.

Typically, probe 12 is inserted into spinal disc SD from the back side 52 of the spinal disc, that is, through the back of the patient. The discectomy method may additionally comprise, after the moving of probe 12 along path or perimeter 36 to sever prismatic portion 34 from remaining portion 46 along that path or perimeter, orienting probe 12 at an acute angle β with respect to a side or lateral surface 54 or 56 of prismatic portion 34. Distal shaft section 16 of probe 12 is inserted under prismatic portion 34, on a far side 58 thereof opposite rear or back side 52 of spinal disc SD. Probe 12 is ultrasonically vibrated while distal shaft section 16 thereof is located under prismatic portion 34, to thereby sever the far side 58 of prismatic portion 34 at least in part from the remaining portion 46 of spinal disc SD. The removal of prismatic portion 34 of the nucleus pulposus NP from the remainder 46 of disc SD may be accomplished in part by prying or levering the prismatic portion away from the remaining disc material with probe 12.

It is to be noted that subsequent to the removal of prismatic nuclear portion 34, with or without attached annulus section 50, remaining disc material 46 may itself be partially or completely removed in a continuing operation. For instance, probe 12 may be operated to remove some of the remaining disc material 46, as well as soft tissue and cartilage, from one or both of the opposing vertebral end faces VF1 and VF2. This procedure prepares vertebral end face or bone surfaces VF1 and VF2 for receiving, between the bone surfaces, a graft or disc prosthesis such as a fusion cage for rigidly connecting the vertebrae to one another.

As described above, severed portion 50 of the annulus fibrosus AF may be coextensive with prismatic portion 34 of nucleus pulposus NP. In that case, the severing of prismatic portion 34 and the severing of annulus fibrosus area 50 may be effectuated at least in part by the moving of probe 12 along path or perimeter 36 while ultrasonically vibrating the probe.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprises:
   inserting an elongate probe into a spinal disc;
   during the inserting of said elongate probe, ultrasonically vibrating said elongate probe;
   thereafter, while ultrasonically vibrating said elongate probe, moving said elongate probe to sever a volumetric portion of the spinal disc; and
   removing said volumetric portion of the spinal disc from a remaining portion of the spinal disc.

2. The method defined in claim 1 wherein:
   the inserting of said elongate probe is in a direction generally parallel to vertebral end faces adjacent to the spinal disc; and
   said volumetric portion is a prismatic portion, the moving of said elongate probe is executed to sever said prismatic portion.

3. The method defined in claim 2 wherein the moving of said elongate probe includes moving said elongate probe along an endless path or perimeter partially defining said prismatic portion.

4. The method defined in claim 3, further comprising maintaining said elongate probe in substantially parallel relation to the vertebral end faces during the moving of the elongate probe along said endless path or perimeter.

5. The method defined in claim 4 wherein said endless path or perimeter extends at least in part in an annulus fibrosus of the spinal disc, so that said prismatic portion includes at least some of said annulus fibrosus and some of a nucleus pulposus of the spinal disc.

6. The method defined in claim 4 wherein said endless path or perimeter extends mainly in a nucleus pulposus of the spinal disc, said prismatic portion including mostly a portion of the nucleus pulposus.

7. The method defined in claim 3 wherein the moving of said elongate probe to sever said prismatic portion is effectuated at least in part by moving said elongate probe along said endless path or perimeter while ultrasonically vibrating said elongate probe.

8. The method defined in claim 3 wherein the inserting of said elongate probe occurs from one side of the spinal disc, further comprising:
   after the moving of said elongate probe along said endless path or perimeter to sever said prismatic portion from said remaining portion along said endless path or perimeter, orienting said elongate probe at an acute angle with respect to a lateral surface of said prismatic portion;
   inserting a distal shaft section of said elongate probe under said prismatic portion, on a far side thereof opposite said one side of the spinal disc; and
   ultrasonically vibrating said elongate probe while said distal shaft section is under said prismatic portion, thereby severing said far side of said prismatic portion at least in part from said remaining portion.

9. The method defined in claim 8 wherein said elongate probe is an asymmetric dissector-shaver having:
   a proximal shaft section;
   a distal shaft section angled relative to said proximal shaft section; and
   a head extending from a distal end of said distal shaft section laterally relative to said distal shaft section, said head having a distal end surface provided with knurls or teeth.

10. The method defined in claim 9 wherein said distal shaft section is provided along an outer surface with at least one energy concentrating projection.

11. The method defined in claim 10 wherein said at least one energy concentrating projection includes a spiral rib.

12. The method defined in claim 1 wherein said volumetric portion includes a portion of an annulus fibrosus of the spinal disc and a portion of a nucleus pulposus of the spinal disc so that said portion of the annulus fibrosus is attached to said portion of the nucleus pulposus and is removed therewith from said remaining portion of the spinal disc.

13. The method defined in claim 12 wherein said portion of the annulus fibrosus is coextensive with said portion of the nucleus pulposus.

14. The method defined in claim 13 wherein the severing of said prismatic portion and the severing of said portion of the annulus fibrosus are effectuated at least in part by the moving of said elongate probe along a path or perimeter while ultrasonically vibrating said elongate probe.

15. The method defined in claim 1 wherein said elongate probe is an asymmetric dissector-shaver having:
   a proximal shaft section;
   a distal shaft section angled relative to said proximal shaft section; and
   a head extending from a distal end of said distal shaft section laterally relative to said distal end section.

16. The method defined in claim 15 wherein said head has a distal end surface provided with knurls or teeth, said distal shaft section being provided along an outer surface with at least one energy concentrating projection.

17. The method defined in claim 16 wherein said at least one energy concentrating projection includes a spiral rib.

18. The method defined in claim 1, further comprising maintaining said elongate probe in substantially parallel relation to vertebral end faces while moving said elongate probe to sever said volumetric portion.

\* \* \* \* \*